US008153081B2

United States Patent
Kuriger

(10) Patent No.: US 8,153,081 B2
(45) Date of Patent: Apr. 10, 2012

(54) TEST SENSOR AND METHOD FOR MANUFACTURING THE SAME

(75) Inventor: Rex J. Kuriger, Granger, IN (US)

(73) Assignee: Bayer Healthcare LLC, Tarrytown, NY (US)

( * ) Notice: Subject to any disclaimer, the term of this patent is extended or adjusted under 35 U.S.C. 154(b) by 1131 days.

(21) Appl. No.: 10/845,026

(22) Filed: May 14, 2004

(65) Prior Publication Data

US 2004/0241881 A1    Dec. 2, 2004

Related U.S. Application Data

(60) Provisional application No. 60/473,703, filed on May 29, 2003.

(51) Int. Cl.
*B44C 1/165* (2006.01)
*B29C 37/00* (2006.01)
*G01N 21/00* (2006.01)
*G01N 15/06* (2006.01)
*G01N 31/22* (2006.01)
*C12Q 1/00* (2006.01)
*C12M 1/34* (2006.01)
*C12M 3/00* (2006.01)

(52) U.S. Cl. ........ 422/420; 156/250; 156/251; 156/230; 156/232; 422/68.1; 422/401; 422/421; 422/425; 435/4; 435/287.1; 435/287.7; 435/287.8; 435/287.9; 435/288.7

(58) Field of Classification Search .................. 156/250, 156/251, 230, 232; 422/58, 60, 56, 57, 68.1, 422/401, 420, 425; 435/4, 287.1, 287.7, 435/287.8, 287.9, 288.7
See application file for complete search history.

(56) References Cited

U.S. PATENT DOCUMENTS

| 4,761,381 | A | 8/1988 | Blatt et al. |
| 4,876,067 | A | 10/1989 | Deneke et al. |
| 4,935,346 | A | 6/1990 | Phillips et al. ................ 435/14 |
| 5,049,487 | A | 9/1991 | Phillips et al. ................ 435/4 |
| 5,304,468 | A | 4/1994 | Phillips et al. ................ 435/14 |
| 5,472,671 | A | 12/1995 | Nilsson et al. |

(Continued)

FOREIGN PATENT DOCUMENTS

EP    0269240 A1    6/1988

(Continued)

OTHER PUBLICATIONS

European Search Report for Application No. 10172250.2, 8 pages, Mar. 15, 2011.

*Primary Examiner* — Mark Shibuya
*Assistant Examiner* — Erik B Crawford
(74) *Attorney, Agent, or Firm* — Nixon Peabody LLP

(57) ABSTRACT

According to one embodiment of the present invention, an optical-based test sensor for use in the determination of an analyte in a liquid sample is disclosed. The test sensor includes a base, a polymer carrier, and a test membrane. The base has a capillary channel formed in a surface of the base that is adapted to move a liquid sample from an inlet to a reaction area formed in the base. The polymer carrier has a lower surface adhered to the surface of the base and is disposed over at least a portion of the capillary channel. The test membrane, which contains a reagent, is adhered to the lower surface of the polymer carrier and extends from the polymer carrier into the reaction area.

23 Claims, 10 Drawing Sheets

U.S. PATENT DOCUMENTS

| | | | |
|---|---|---|---|
| 5,520,883 A | 5/1996 | Charlton et al. | |
| 5,611,999 A | 3/1997 | Dosmann et al. | |
| 5,679,311 A | 10/1997 | Harttig et al. | 422/102 |
| 5,700,695 A | 12/1997 | Yassinzadeh et al. | |
| 5,723,284 A | 3/1998 | Ye | |
| 5,814,522 A | 9/1998 | Zimmer et al. | |
| 5,843,691 A * | 12/1998 | Douglas et al. | 435/14 |
| 5,962,215 A | 10/1999 | Douglas et al. | |
| 6,036,919 A | 3/2000 | Thym et al. | 422/58 |
| 6,156,270 A | 12/2000 | Buechler | |
| 6,206,841 B1 | 3/2001 | Cunningham et al. | 600/584 |
| 6,207,000 B1 | 3/2001 | Schwobel et al. | 156/248 |
| 6,300,138 B1 | 10/2001 | Gleason et al. | |
| 6,368,563 B1 | 4/2002 | Allen et al. | |
| 6,403,037 B1 | 6/2002 | Chang et al. | |
| 6,403,384 B1 | 6/2002 | Lea | |
| 6,531,322 B1 * | 3/2003 | Jurik et al. | 436/95 |
| 6,818,180 B2 * | 11/2004 | Douglas et al. | 422/58 |
| 6,949,297 B2 * | 9/2005 | Yang et al. | 428/520 |
| 6,986,869 B2 * | 1/2006 | Tuohy et al. | 422/56 |
| 7,008,799 B1 * | 3/2006 | Zimmer et al. | 436/514 |
| 2002/0168290 A1 | 11/2002 | Yuzhakov et al. | |
| 2003/0007893 A1 | 1/2003 | Purcell | |
| 2004/0028558 A1 * | 2/2004 | Pollock et al. | 422/57 |
| 2004/0161365 A1 * | 8/2004 | Siu Yu | 422/56 |

FOREIGN PATENT DOCUMENTS

| | | |
|---|---|---|
| EP | 0483117 A2 | 4/1992 |
| EP | 0974840 A2 | 1/2000 |
| EP | 1 203 823 A1 | 5/2002 |
| EP | 1223425 | 7/2002 |
| EP | 0443231 A1 | 11/2009 |
| JP | 5157745 A | 6/1993 |
| JP | 10191995 A | 7/1998 |
| JP | 10197526 A | 7/1998 |
| JP | 2001272399 A | 10/2001 |

* cited by examiner

TEST SENSOR AND METHOD FOR MANUFACTURING THE SAME

CROSS-REFERENCE TO RELATED APPLICATION

This application claims the benefit of U.S. Provisional Application 60/473,703, filed on May 29, 2003, which is hereby incorporated by reference in its entirety.

FIELD OF THE INVENTION

The present invention relates generally to liquid sample monitoring devices and, more particularly, to the manufacture and design of a test sensor for use in determining the concentration of an analyte in a liquid sample.

BACKGROUND OF THE INVENTION

Test sensors are often used in assays for determining the concentration of an analyte in a liquid sample. A liquid sample is deposited in a reaction area of the test sensor that includes a reagent. The sample and the reagent mix produce a measurable reaction indicating the concentration of the analyte in the liquid sample. The reaction is measured with a test device that receives the test sensor.

Testing for the concentration of glucose in blood is a common use for test sensors. Those who have irregular blood-glucose concentration levels are often medically required to self-monitor their blood-glucose concentration level. Utilizing a testing device that implements a test sensor is one means that people use to monitor their blood-glucose concentration levels. Test sensors are also used for determining the concentration of or determining the presence of various other analytes (e.g., fructosamine, hemoglobin, cholesterol, glucose, alcohol, drugs, etc.) in a variety of body fluids (e.g., blood, interstitial fluid, saliva, urine, etc.). Test sensors including appropriate reagents can be used in the harvesting of most any liquid sample for the determination of the concentration of an analyte in that sample.

The type of reagent implemented in the test sensor depends on the type of measuring used. For example, in a colorimeteric assay, the color change of a reaction area containing a reagent following contact with the sample is measured to determine the concentration of the analyte of interest in the sample. The degree of color change is measured using an optical sensor(s) that converts the degree of color change to electrical signals that are evaluated with diagnostic equipment. For example, the optical device may measure the amount of light reflected from, or transmitted through, the reaction area. In other embodiments of the present invention, the amount of infrared light absorbed by the reaction of the analyte in the sample and the reagent is measured. Colorimetric testing is described in detail in U.S. Pat. No. 5,723,284 entitled "Control Solution and Method for Testing the Performance of an Electrochemical Device for Determining the Concentration of an Analyte in Blood," which is incorporated herein by reference in its entirety. Colorimetric testing is also described in detail in U.S. Pat. Nos. 6,181,417 B1 (entitled "Photometric Readhead with Light Shaping Plate"), 5,518,689 (entitled "Diffuse Light Reflectance Readhead"), and 5,611,999 (entitled "Diffuse Light Reflectance Readhead"), each of which is incorporated herein by reference in its entirety.

The reagent that is used in the test sensor is a chemical agent that is costly to produce. Thus, it is desirable to limit the amount of reagent used and to reduce any waste of the reagent. Current manufacturing processes waste the costly reagent by impregnating more test membrane material than necessary. The test sensors include a membrane that is impregnated with the reagent during manufacturing by dipping, which entails submerging a test membrane sheet in the reagent. Test sensor disks (i.e., cut sections sized for inclusion in a test sensor) are cut from the impregnated membrane sheet which results in wasted portions of the reagent impregnated sheet. Further, picking and placing the reagent impregnated sensor disks into the test sensor introduces material handling issues due to the sensitivity of the reagent which impacts the complexity and cost of the test sensor manufacturing process.

SUMMARY OF THE INVENTION

According to one embodiment of the present invention, an optical-based test sensor for use in the determination of an analyte in a liquid sample is disclosed. The test sensor includes a base, a polymer carrier, and a test membrane. The base has a capillary channel formed in a surface of the base that is adapted to move a liquid sample from an inlet to a reaction area formed in the base. The polymer carrier has a lower surface adhered to the surface of the base and is disposed over at least a portion of the capillary channel. The test membrane, which contains a reagent, is adhered to the lower surface of the polymer carrier and extends from the polymer carrier into the reaction area.

The above summary of the present invention is not intended to represent each embodiment, or every aspect, of the present invention. Additional features and benefits of the present invention will become apparent from the detail description, figures, and claims set forth below.

Figure 1:
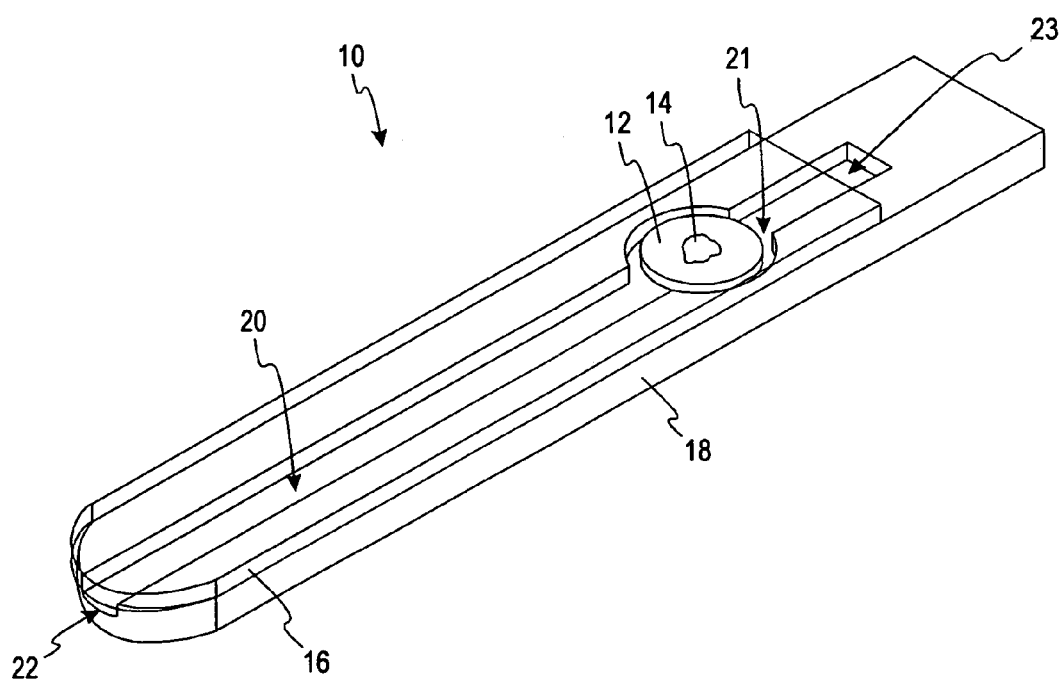
FIG. 1 is a perspective view of a test sensor according to one embodiment of the present invention.

While the invention is susceptible to various modifications and alternative forms, specific embodiments will be shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DESCRIPTION OF ILLUSTRATED EMBODIMENTS

Turning now to the drawings and initially to FIG. 1, a test sensor 10 is shown according to one embodiment of the present invention. The test sensor 10 is used in the harvesting and analysis of a liquid sample for determining the presence or concentration of an analyte in the liquid sample. The test sensor 10 includes a test membrane disk 12 having a reagent 14 disposed therein. The test membrane disk 12 is adhered to the underside (as viewed in FIG. 1) of a carrier strip 16. The carrier strip 16 is laminated to a base 18 of the test sensor such that the test membrane disk 12 downwardly extends into a reaction area 21 of a capillary channel 20 formed in the base 18. The carrier strip 16 forms a lid over the capillary channel 20.

When conducting an assay, a liquid sample is harvested by positioning an inlet 22 of the capillary channel 20 adjacent the sample. The sample is moved, via capillary action, from the inlet 22 to the reaction area 21 where an analyte in the sample reacts with the reagent disposed in the test membrane 12. Optionally, the carrier 16 is positioned on the base 18 such that the upstream end of the capillary channel 20 remains uncovered to form a vent 23 to facilitate movement of the fluid sample in the capillary channel. Once the sample is moved into the reaction area, the analyte of interest (e.g., glucose) reacts with the reagent 14 on the test membrane disk 12 and that reaction is measured with an optical device as previously described in the Background Section.

According to one embodiment of the present invention, the capillary channel 20 is sized to provide underfill protection so that a required volume of sample is delivered to the reaction area 21. Additionally, or alternatively, the capillary channel 20 is widened to increase the lateral flow of the sample to the test membrane disk 12 by enlarging the surface area of the test membrane disk 12 periphery exposed to the sample flow in the capillary channel 20. In yet other embodiments, the base 18 is dimensioned to create a small gap between the side walls of the capillary channel 20 and the edges of the test membrane, the bottom wall of the capillary channel 20 and the bottom surface of the membrane, or both. These gaps provide a clearance to allow the flow of the sample across the bottom surface and edges of the test membrane disk 12, which decreases saturation time and uniformity of the assay. These gaps between the edge and bottom of the test membrane disk 12 and the capillary channel 20 can range between about 0.0005 inch (about 0.0127 mm) and about 0.001 inch (about 0.0254 mm). In other alternative embodiments, a wicking membrane or mesh is attached to the test membrane 12 to draw and diffuse the sample across the test membrane 12 to increase the flow of the sample across the test membrane disk 12.

According to one embodiment of the present invention, the test membranes 12 are made of a hydrophilic polyethersulfone material having pore sizes ranging from about 0.2 to about 8 micrometers. The Presense membrane and the Predator® membrane, both manufactured by Pall Specialty Materials of Port Washington, N.Y., are two examples of commercially available test membranes that may be used in various embodiments of the present invention. Alternatively, the test membrane may be made of a nitrocellulose material. While the test membrane disks 12 shown in FIG. 1 are disk-shaped, the test membranes can be of any shape in alternative embodiments of the present invention.

The carrier 16 and the base 18 are both constructed of plastic. According to one embodiment of the present invention, the carrier 16 and the base 18 are constructed of plastic having a surface tension of less than about 45 milli-Newtons per meter such as polystyrene, polypropylene, polyethylene, polyethylene terephthalate, polycarbonate, and polyvinyl chloride, for example. The carrier 16 and base 18 are constructed of a somewhat hydrophobic material so as not to absorb the reagent 14 or the sample that moves through the capillary channel 20 formed in the base 18 according to one embodiment of the present invention. Further, these materials are not adversely affected by the liquid samples (e.g., blood, urine, or saliva) to be tested. The carrier 16 is substantially optically transparent allowing the reaction between the analyte in the sample and the reagent to be optically measured through the carrier 16.

The dimensions of the test sensor 10 according to one embodiment of the present invention are as follows. The capillary channel 20 has a width ranging between about 1 mm and about 2 mm, with the reaction area 21 having a diameter of about 3-5 mm. The test membrane disk 12 has a diameter of about 2.5 to about 3.5 mm. In other embodiments, the test membrane disk 12 has a diameter of about 1 to about 2 mm, the reaction area 21 has a diameter of about 1.5 to about 2.5 mm, and the capillary channel 20 has a width of 0.75 to about 1 mm. The reaction area 21 has a depth of about 0.10 to about 0.20 mm, leaving clearance between the bottom surface of the reaction area 21 and the test membrane disk 12. This clearance increases fluid sample flow across the bottom surface of the test membrane disk 12.

Figure 2:
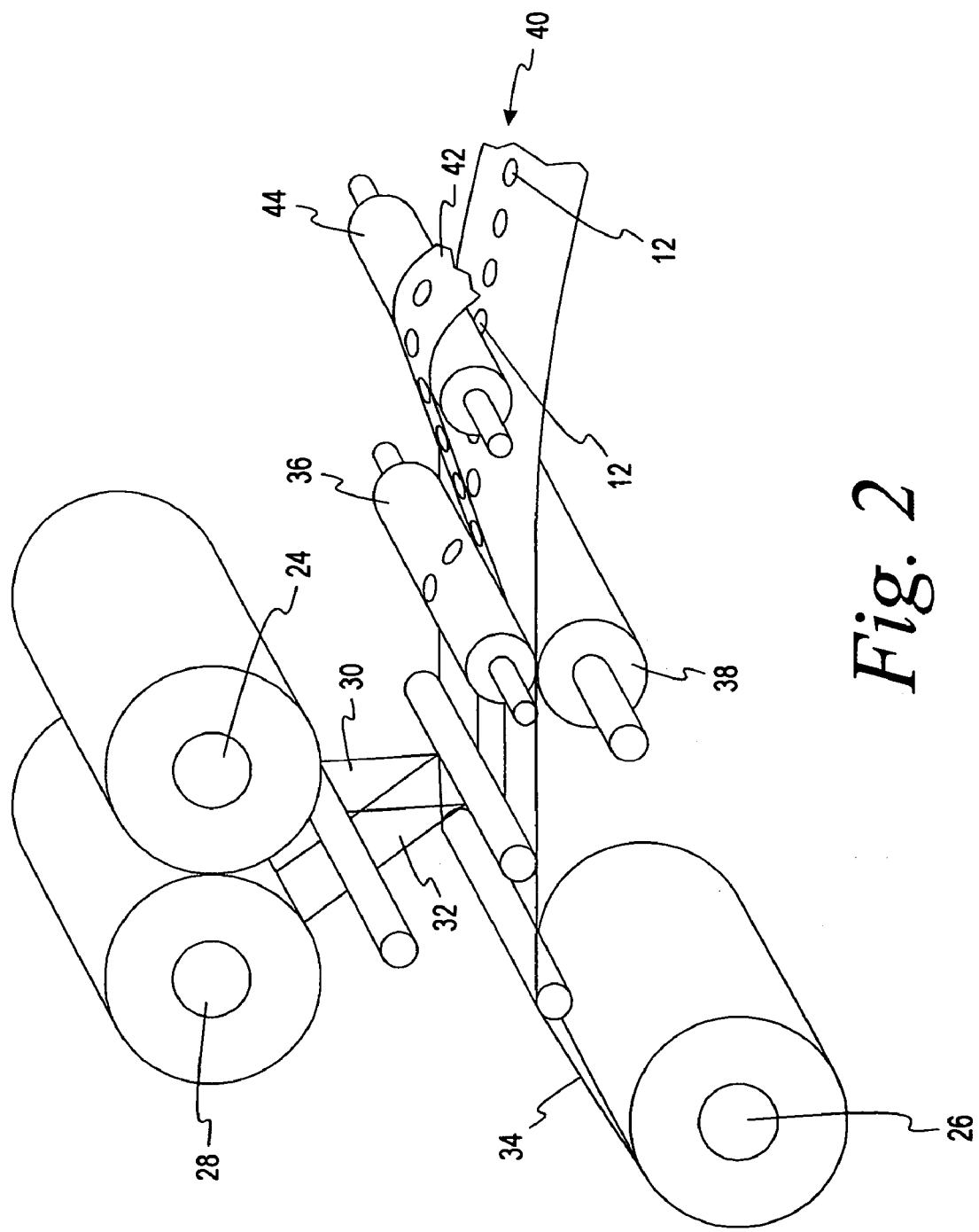
FIG. 2 is a perspective view of a system for manufacturing test membranes according to one embodiment of the present invention.

Referring also to FIG. 2, a method of manufacturing the test sensor 10 according to one embodiment of the present invention will be described. The membrane material (i.e., the material from which test membrane disks 12 are cut) and the carrier material (i.e., the material from which the carrier 16 is cut) are stored on a first roll 24 and a second roll 26, respectively. An adhesive liner, for adhering the membrane material to the carrier material, is disposed on a third roll 28. The adhesive liner that adheres the test membrane disk 12 to the carrier 16 (formed from the carrier web 34) comprises a substantially optically clear adhesive for permitting the test membrane disk 12 to be read through the substantially optically clear carrier 16. A test membrane web 30 from the first roll 24, an adhesive liner web 32 from the third roll 28, and a carrier web 34 from the second roll 26 are fed between a cylindrical, rotating die 36 and counter pressure roller 38 that crush-cut the test membrane web 30 and the adhesive liner web 32 onto the carrier web 34. The carrier web 34 is not cut resulting in a continuous membrane/carrier strip 40 having individual, cut test membrane disks 12 adhered thereto and spaced apart by a predetermined distance. The excess adhesive liner material and test membrane material 42 are lifted from the membrane/carrier strip 40 by a withdraw roller 44.

Figure 3A:
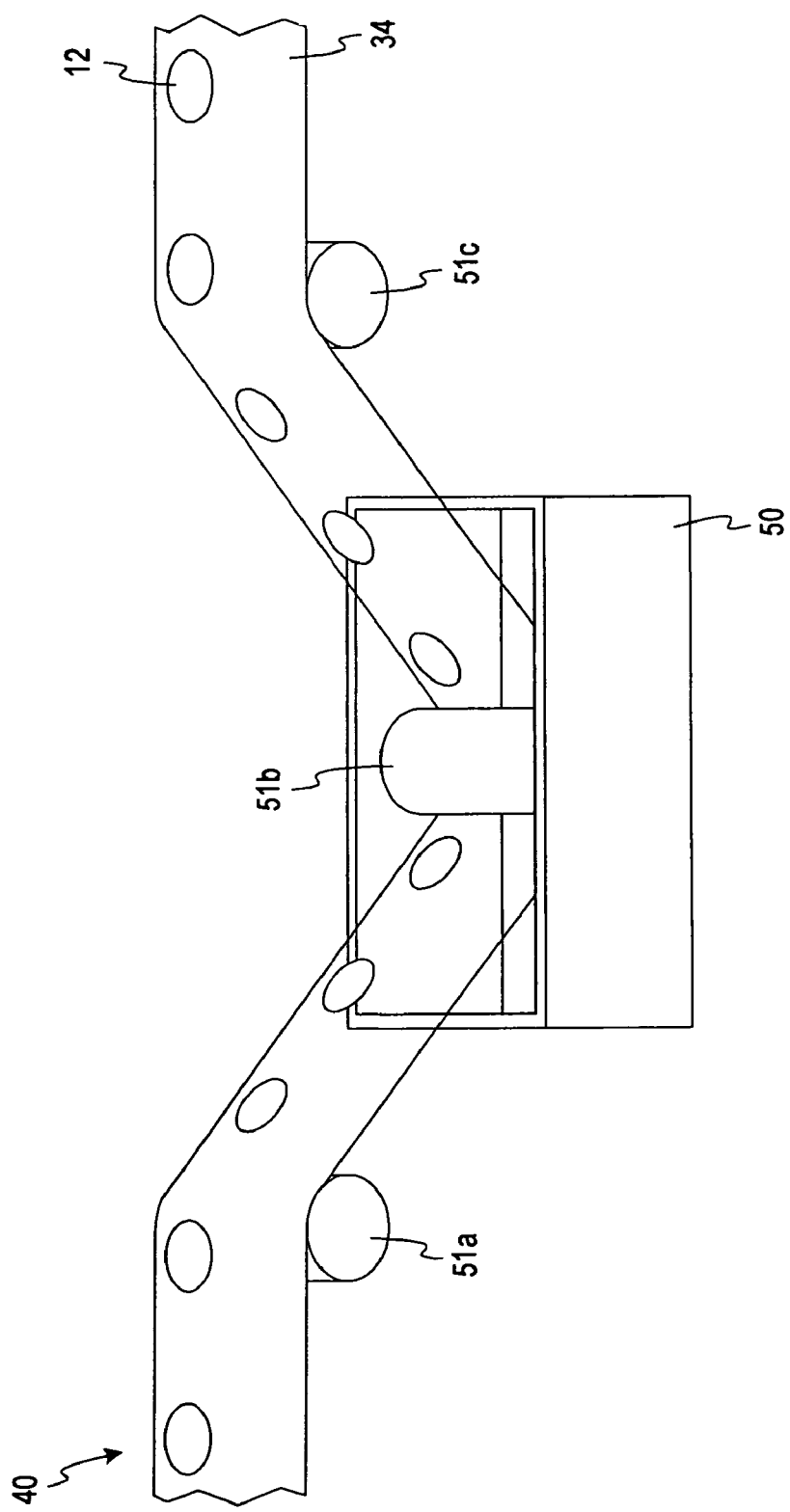
FIG. 3a is a perspective view of dipping system for applying a reagent to a test membrane according to one embodiment of the present invention.

Turning now to FIG. 3a, the membrane/carrier strip 40 is dipped into a tank 50 containing a liquid reagent for impregnating the test membrane disks 12 with the reagent 14. As the membrane/carrier strip 40 is directed into the tank 50, via a plurality of rollers 51a-c, the test membrane disks 12 absorb the reagent 14. The carrier 34 does not absorb any of the reagent 14 due to its hydrophobic nature. Thus, only the test membrane disks 12 absorb the reagent 14.

Only the portions of the membrane material to be used (e.g., the test membrane disks 12) and not any excess membrane material absorb the costly reagent because the test membrane disks 12 have been cut to the appropriate size for insertion into a test sensor base 18 (FIG. 1) prior to being impregnated with the reagent. In addition to the size of the test membranes 12, further measures may be implemented for controlling the amount of reagent 14 absorbed by the test membrane disks 12 in alternative embodiments of the present invention. The speed at which the membrane/carrier strip 40 is advanced into the tank 50 of reagent 14 can be varied to control the amount of time each test membrane disks 12 spends dipped in the reagent 14. The degree of impregnation of each test membrane disk 12 is directly proportional to the amount of time that the test membrane disk 12 is dipped into the reagent 14. Additionally, apertures may be formed in the carrier web 34 so that the test membrane disks 12 absorb the reagent 14 from both sides. In such an embodiment, the time in which each test membrane disk 12 is dipped into the reagent 14 may be decreased because each test membrane disk 12 is absorbing reagent 14 from both sides which increases the test membrane disk's 12 rate of reagent 14 absorption.

Figure 3B:
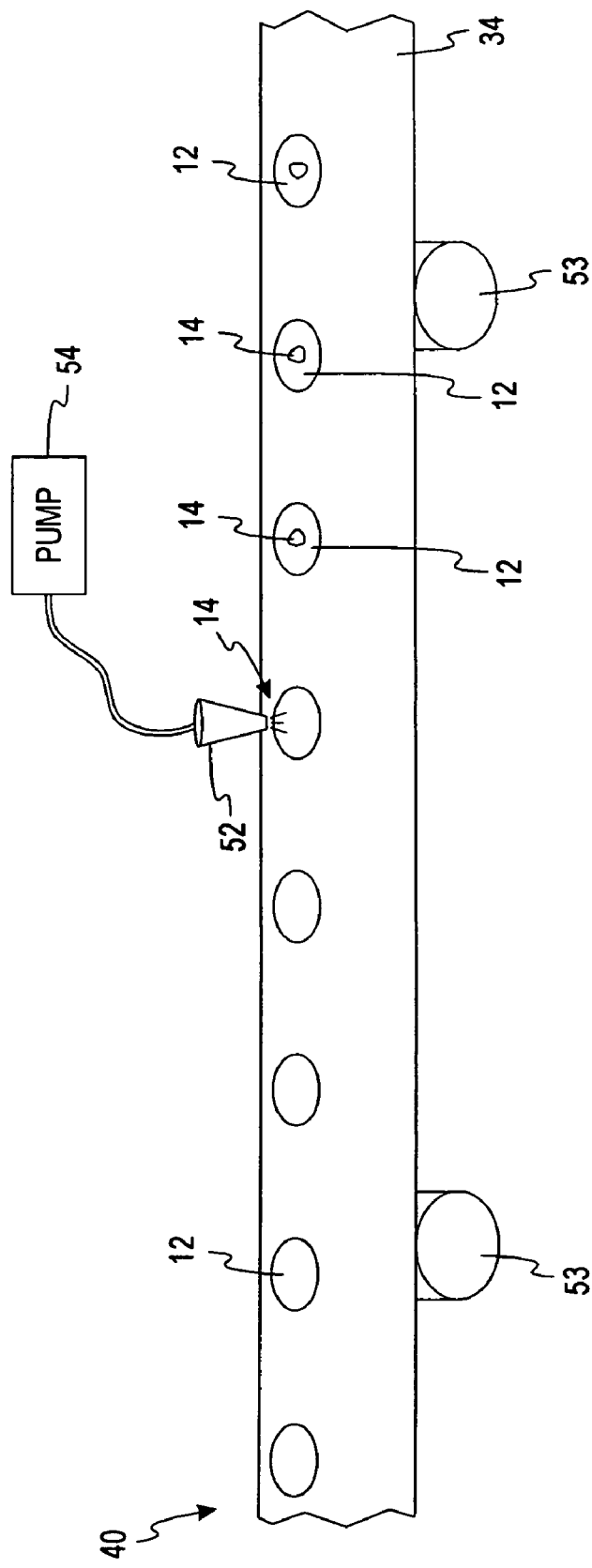
FIG. 3b is a perspective view of pumping system for applying a reagent to a test membrane according to an alternative embodiment of the present invention.

Referring to FIG. 3b, an alternative embodiment for disposing the reagent 14 on the test membrane disks 12 is illustrated. The membrane/carrier strip 40 is moved past a nozzle 52, via a plurality of rollers 53, that is in fluid communication with a pump 54 for pumping the reagent 14 though the nozzle 52. The nozzle 52 directs the reagent 14 onto the test membrane disks 12. The pump 54 controls the amount of reagent 14 deposited on each test membrane disk 12.

Figure 4:
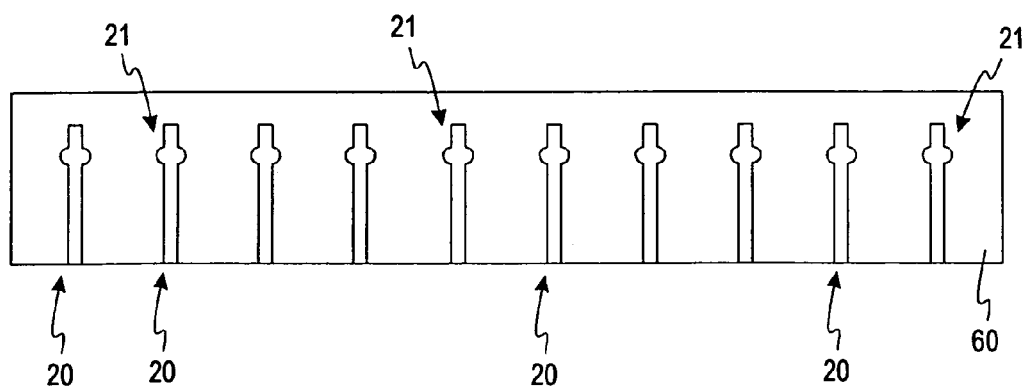
FIG. 4 is a top perspective view of a substrate having a plurality of capillary channels formed therein according to one embodiment of the present invention.

Referring to FIG. 4, a polymer substrate 60 is provided from which the test sensor bases 18 (FIG. 1) are formed. As discussed above, the bases 18 are constructed of a polymer material so that the liquid sample to be analyzed is not absorbed by the test sensor base 18. A plurality of capillary channels 20, including the reaction areas 21, are formed in the polymer substrate 60. The capillary channels 20 are formed in the substrate 60 by any one of a variety of known manufacturing processes including flat bed embossing or rotary embossing. The process of embossing the capillary channel 20 into the polymer substrate 60 is performed using a continuous web process, similar to the method described above for cutting the test membrane disks 12 from the web of membrane material 12 (FIG. 2). A long length of the substrate may be formed in a reel format or in a sheet format having a specific number (e.g., 5, 10 or 20) of capillary channels formed therein.

Figure 5:
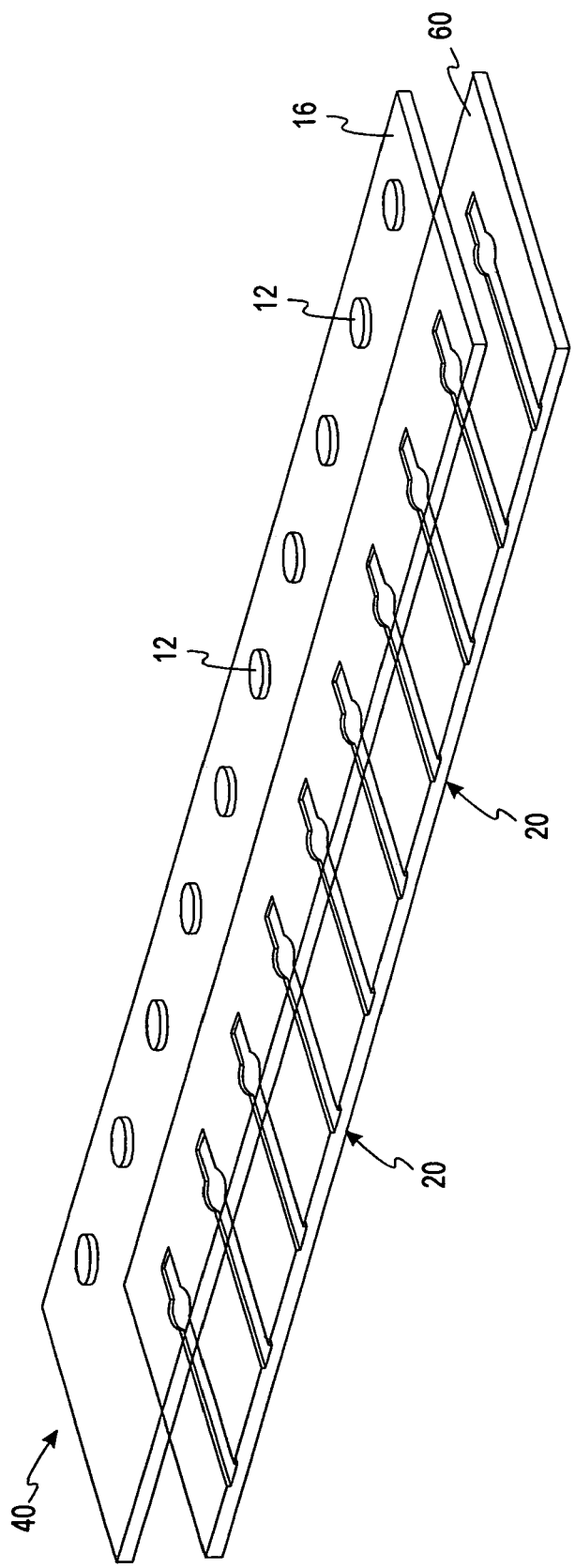
FIG. 5 is a perspective view of a plurality of test membrane disks attached to a carrier and a substrate having a plurality of capillary channels formed therein according to one embodiment of the present invention.

Referring to FIG. 5, the polymer substrate 60 having the capillary channels 20 formed therein is attached to the membrane/carrier strip 40 comprising the carrier 16 and the plurality of test membrane disks 12 disposed thereon. The membrane/carrier strip 40 is disposed on the polymer substrate 60 such that the test membrane disks 12 extends into the reaction areas 21 of the capillary channels 20 formed in the polymer substrate 60. The membrane/carrier strip 40 is laminated to the substrate 60 using an adhesive. According to alternative embodiments of the present invention, the adhesive may be applied to the polymer substrate 60 prior to or subsequent to forming the capillary channels 20 in the substrate 60. According to one embodiment of the present invention, the adhesive used to laminate the membrane/carrier strip 40 to the polymer substrate is heat and pressure sensitive. An example of an adhesive for use with the present invention is described in U.S. Pat. Nos. 5,759,364 and 5,798,031, each of which is incorporated herein by reference in its entirety.

Figure 6:
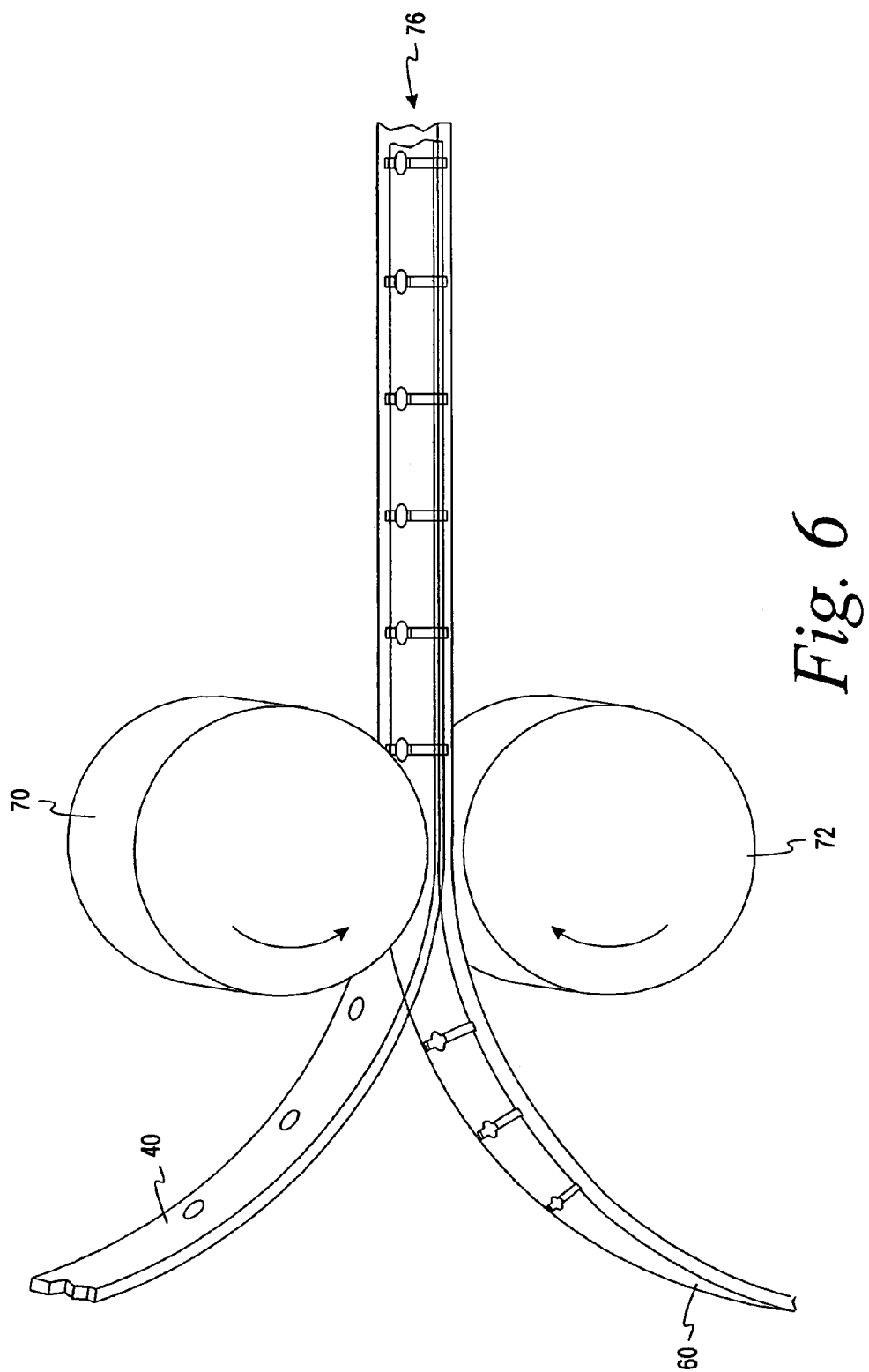
FIG. 6 is a perspective view of a system for laminating the test membrane disks attached to a carrier to a substrate having a plurality of capillary channels formed therein according to one embodiment of the present invention.

Referring to FIG. 6, a continuous process for laminating the membrane/carrier strip 40 to the polymer substrate 60 is illustrated according to one-embodiment of the present invention. The substrate 60 and the membrane/carrier strip 40 are fed between a pair of rollers 70, 72 for continuously laminating the substrate 60 and the membrane/carrier strip 40 together. For example, according to one embodiment of the present invention, the capillary channels 20 are formed in a length of substrate 60 that is fed between rollers 70, 72 along with the membrane/carrier strip 40, wherein the membrane/carrier strip 40 is fed directly from the dipping process illustrated in FIG. 2 for forming a continuous length 76 of test sensors 10. Alternatively, non-continuous sheets of test sensors 10 (e.g., 5, 10, or 15 test sensors) such as shown in FIG. 5, are laminated to a substrate 60 having the same number of capillary channels 20 formed therein.

Figure 7:
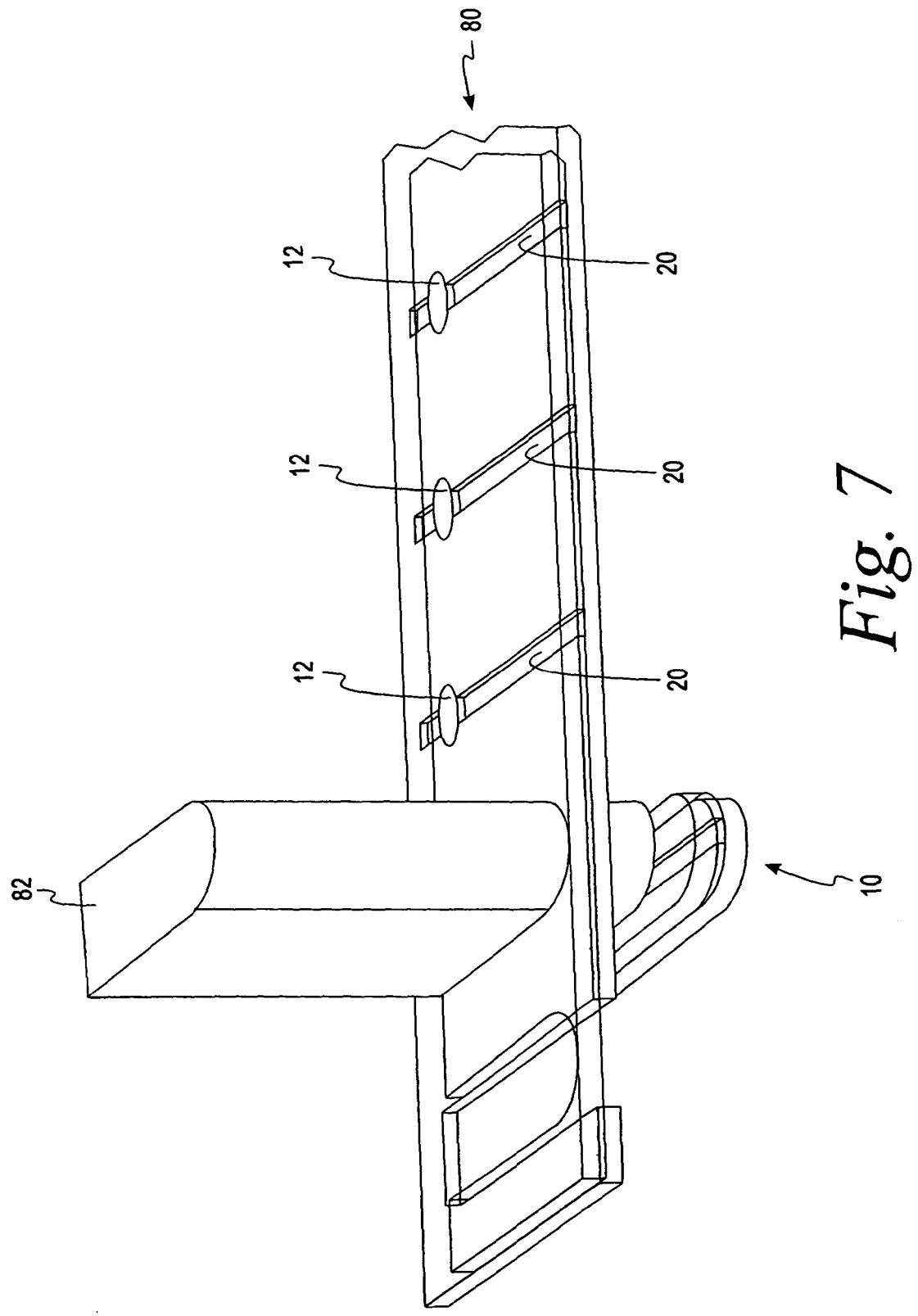
FIG. 7 is a perspective view of a stamping system for cutting a test sensor from a sheet of test sensors according to one embodiment of the present invention.

Referring to FIG. 7, individual test sensors 10 are cut from a length 80 a plurality of test sensors 10. According to the illustrated embodiment, the test sensors 10 are cut from the length 80 of test sensors 10 using a stamping process. The length 80 is fed into a stamping die 82 which contains a die to cut out the individual test sensors 10. After stamping, the individual test sensors are packaged. In an alternative embodiment, the test sensors 10 are cut from the length 80 of test sensors 10 using a blade, rather than a stamping die.

As indicated in the discussion above, the manufacturing steps described in connection with FIGS. 2-7 may be part of a continuous manufacturing process wherein the stages are disposed along an manufacturing line. For example, the membrane/carrier strip 40 formed as described in connection with FIG. 2 may be fed directly into the reagent tank 50 discussed in connection with FIG. 3a, or past the nozzle as described in connection with FIG. 3b. Alternatively, the various manufacturing stages of FIGS. 2-7 may be implemented in a non-continuous processes. For example, a reel of the membrane/carrier strip 40 may be formed (FIG. 2) and then that reel is later fed into the reagent tank 50 discussed in connection with. FIG. 3a.

According to an alternative embodiment of the present invention, the reagent is applied to the test membrane disks 12 of the test sensors 10 by pumping the reagent 14 onto the test membrane disks 12. In such an embodiment, the test membranes disks 12 are die-cut onto the polymer carriers 16 as described above in connection with FIG. 2. However, instead of dipping the carrier/membrane strip 40 into the reagent tank 50 as described in connection with FIG. 3a, the carrier/membrane strip 40 is advanced past a reagent pump 54 as illustrated in FIG. 3b for depositing a predetermined amount of reagent 14 onto each of the test membrane disks 12. This method is also advantageous because the amount of reagent 14 deposited onto each test membrane 12 is controlled by the pump. In another embodiment of the present invention, the reagent is deposited or "ink-jetted" onto the test membranes by use of a plurality of piezoelectric controlled nozzles as are commonly used for depositing ink on paper in ink jet printers.

While the test sensor 10 has been described thus far as having a two piece construction (i.e., a base 18 and a carrier 16) with the capillary channel 20 formed in the base, the test sensor can have a three piece construction with the capillary channel cut in a middle piece in alternative embodiments of the present invention. For example, a flat base, a generally U-shaped middle layer, and a flat lid are adhered together. The side walls of the capillary channel are formed by the interior of the U-shaped middle layer. A test membrane disk, which is attached to the lid as described in connection with FIG. 1, is positioned within the closed end of the U-shaped middle layer and the open end of the U-shaped middle layer forms the inlet of the capillary channel.

Figure 8:
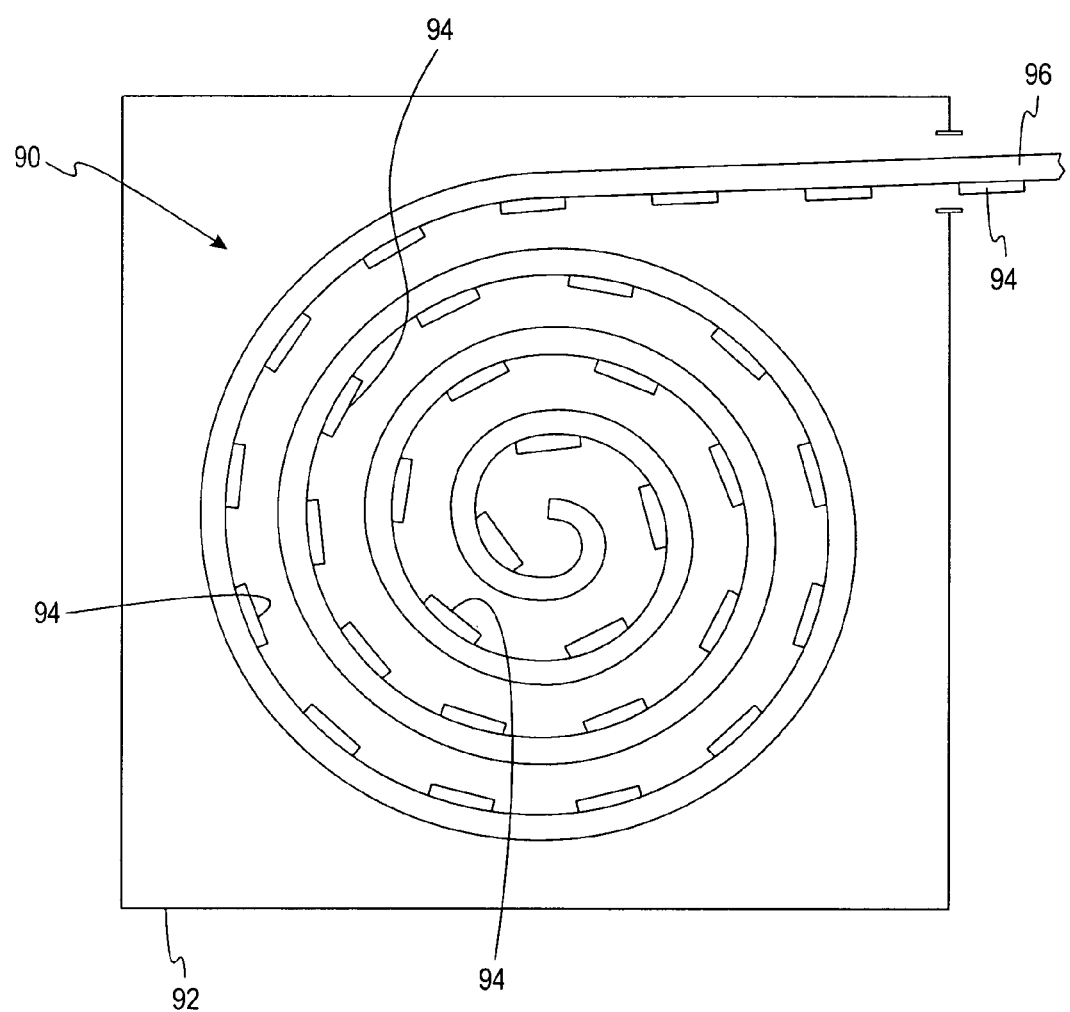
FIG. 8 is a side view of a cartridge having a reel of test membranes disposed therein according to an alternative embodiment of the present invention.

Referring to FIG. 8, in another embodiment of the present invention, a reel 90 of the membrane/carrier strip 40 formed as described in connection with FIG. 2 is disposed with a dispensing cartridge 92 for dispensing test membrane disks 94 impregnated with a reagent attached to a carrier 96 one at a time. According to one embodiment of the present invention, the cartridge 92 includes a cutting means (e.g., a sharp or serrated edge) for cutting the carrier 96 for dispensing one test membrane disk 94 at a time. Alternatively, the carrier 96 is perforated between test membrane disks 94 during manufacturing to facilitate the tearing off of a single test membrane disk 94 from the reel 90. The individually dispensed test membrane disks 94 can be used with a top-fill device for determining the concentration of an analyte in a liquid sample according to an alternative embodiment of the present invention.

Figure 9:
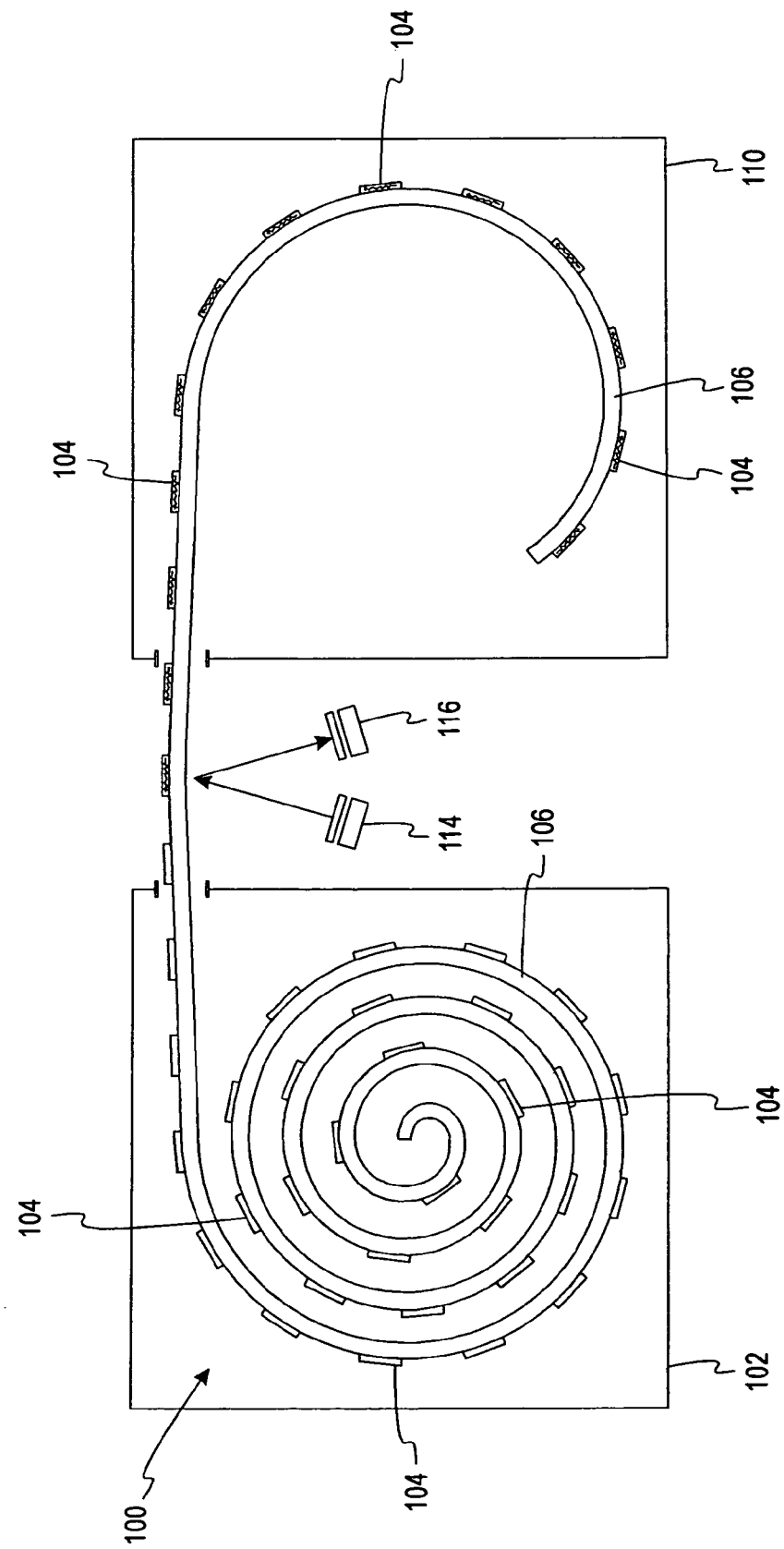
FIG. 9 is a side view of a dispensing cartridge having a reel of test membranes disposed therein and a collecting cartridge according to another alternative embodiment of the present invention.

Referring to FIG. 9, in another embodiment of the present invention, a reel 100 of the membrane/carrier strip 40 formed as described in connection with FIG. 2 is disposed with a dispensing cartridge 102 for dispensing test membrane disks 104 impregnated with a reagent attached to a carrier 106 one at a time, similar to that described in connection with FIG. 8. A collecting cartridge 110 collects the used test membrane disks 104. According to one embodiment, the dispensing and collecting cartridges 102 and 110 are implemented in a top-fill blood monitoring device wherein, for a example, a user places a blood sample (or other body fluid sample) on a test membrane disk 104 dispensed from the dispensing cartridge 102. The top-fill device includes a light source 114 for illuminating the test membrane disk having a sample deposited thereon and a light detector 116 for measuring light reflected from the reaction of the analyte in the body fluid and the reagent on the test membrane disk 12 as is known in the art for determining the concentration of the analyte in the body fluid.

While the invention is susceptible to various modifications and alternative forms, specific embodiments thereof have been shown by way of example in the drawings and herein described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

What is claimed is:

1. A test sensor for use in the determination of an analyte in a liquid sample, the test sensor comprising:
   a base defining a bottom wall and a plurality of side walls of a capillary channel and a reaction area formed in a surface of the base, the capillary channel adapted to move a liquid sample from an inlet to the reaction area;
   a carrier having a first surface directly attached to the surface of the base, the carrier being disposed over at least a portion of the capillary channel; and
   a test membrane adhered to the first surface of the carrier such that the test membrane does not contact the bottom wall and the plurality of side walls of the capillary channel and the reaction area defined by the base, the test membrane containing a reagent, the test membrane extending from the carrier into the reaction area.

2. The test sensor of claim 1 wherein the reagent is adapted to produce a colorimetric reaction indicative of the concentration of the analyte in the sample.

3. The test sensor of claim 1 wherein the test membrane is generally disk-shaped.

4. The test sensor of claim 1 wherein the carrier is constructed of a substantially hydrophobic material.

5. The test sensor of claim 1 wherein the carrier is constructed of a substantially optically clear material.

6. The test sensor of claim 1 wherein the test membrane is adhered to the lower surface of the carrier with a substantially optically clear adhesive.

7. The test sensor of claim 1 wherein the test membrane is constructed of a polyethersulfone material.

8. The test sensor of claim 1 wherein the capillary channel has an inlet end and an opposite end, the opposite end being uncovered by the carrier.

9. A test sensor for use in the determination of an analyte in a liquid sample, the test sensor comprising:
   a base defining a bottom wall and a plurality of side walls of a capillary channel and a reaction area formed in a surface of the base, the reaction area having a depth formed in the base, the capillary channel adapted to move a liquid sample from an inlet to the reaction area;
   a carrier having a first surface directly attached to the surface of the base, the carrier being disposed over at least a portion of the capillary channel; and
   a test membrane adhered to the first surface of the carrier, the test membrane containing a reagent, the test membrane extending from the carrier into the reaction area and having a thickness less than the depth of the reaction area such that the test membrane does not contact the base and a first space is provided between a lower surface of the test membrane and a bottom of the reaction area,
   wherein a transverse dimension of the test membrane is less than a transverse dimension of the reaction area such that a second space is provided between an edge of the test membrane and an edge of the reaction area.

10. The test sensor of claim 9, wherein the capillary channel has an inlet end and an opposite end, the opposite end being uncovered by the carrier.

11. The test sensor of claim 9, wherein the reagent is adapted to produce a colorimetric reaction indicative of the concentration of the analyte in the sample.

12. The test sensor of claim 9, wherein the test membrane is adhered to the lower surface of the carrier with a substantially optically clear adhesive.

13. A test sensor for use in the determination of an analyte in a liquid sample, the test sensor comprising:
   a base defining a bottom wall and a plurality of side walls of a capillary channel and a reaction area formed in a surface of the base, the capillary channel adapted to move a liquid sample from an inlet to the reaction area;
   a polymer carrier having a first surface directly attached to the surface of the base, the polymer carrier being disposed over at least a portion of the capillary channel and being constructed of a substantially hydrophobic material; and
   a generally disk-shaped test membrane adhered to the first surface of the polymer carrier such that the test membrane does not contact the bottom wall and the plurality of side walls of the capillary channel and the reaction area defined by the base, the test membrane containing a reagent, the test membrane extending from the polymer carrier into the reaction area.

14. The test sensor of claim 13, wherein the carrier is constructed of a substantially optically clear material.

15. The test sensor of claim 13, wherein the generally disk-shaped test membrane is adhered to the lower surface of the carrier with a substantially optically clear adhesive.

16. The test sensor of claim 13, wherein the generally disk-shaped test membrane is constructed of a polyethersulfone material.

17. The test sensor of claim 13, wherein the reagent is adapted to produce a colorimetric reaction indicative of the concentration of the analyte in the sample.

18. The test sensor of claim 1 wherein the lower surface of the carrier is directly attached to the surface of the base with an adhesive.

19. The test sensor of claim 9, wherein the lower surface of the carrier is directly attached to the surface of the base with an adhesive.

20. The test sensor of claim 1, wherein the carrier is a polymer carrier.

21. The test sensor of claim 9, wherein the carrier is a polymer carrier.

22. The test sensor of claim 1, wherein the sensor is an optical sensor.

23. The test sensor of claim 1, wherein the sensor is an electrochemical sensor.

* * * * *